US00PP36844P2

(12) United States Plant Patent
Mathey

(10) Patent No.: US PP36,844 P2
(45) Date of Patent: Jul. 22, 2025

(54) ***ABELIA* PLANT NAMED 'SMNAMW'**

(50) Latin Name: *Abelia mosanensis*
Varietal Denomination: SMNAMW

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/947,423

(22) Filed: Nov. 14, 2024

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 6/00
See application file for complete search history.

*Primary Examiner* — Keith O. Robinson
(74) *Attorney, Agent, or Firm* — C. Anne Whealy

(57) ABSTRACT

A new and distinct cultivar of *Abelia* plant named 'SMNAMW', characterized by its upright to outwardly spreading and mounding plant habit; moderately vigorous to vigorous growth habit; freely branching habit; dense and bushy appearance; dark green-colored leaves that in the autumn, turn yellow to bright red and burgundy in color; freely flowering habit; strongly fragrant white-colored flowers and reddish pink-colored corolla tubes; and good garden performance.

3 Drawing Sheets

Figure 1:
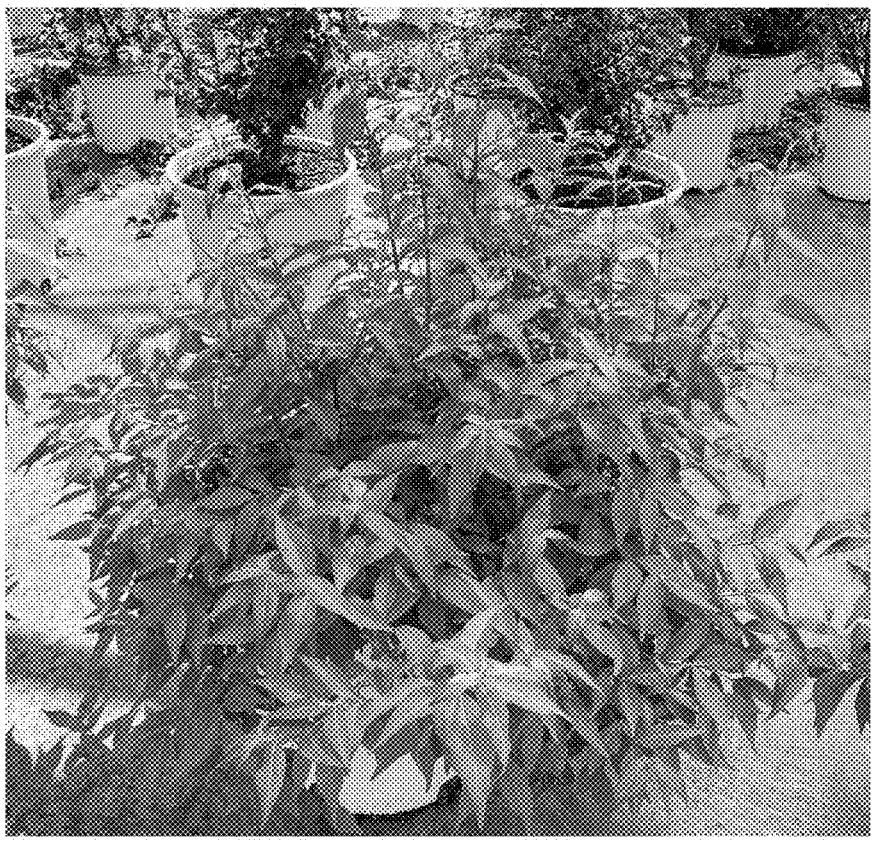

Botanical designation: *Abelia mosanensis.*
Cultivar denomination: 'SMNAMW'.

BACKGROUND OF THE INVENTION

The present invention relates to a new and distinct cultivar of *Abelia* plant, botanically known as *Abelia mosanensis*, commonly referred to as Fragrant *Abelia* and hereinafter referred to by the name 'SMNAMW'

The new *Abelia* is a product of a planned breeding program conducted by the Inventor in Grand Haven, Michigan. The objective of the breeding program was to develop new compact and freely branching *Abelia* plants with attractive and unique leaf coloration.

The new *Abelia* plant originated from an open-pollination during proprietary selection of *Abelia mosanensis* as the male, or pollen, parent. The new *Abelia* plant was discovered and selected by the Inventor during the summer of 2019 as a single flowering plant within the progeny of the stated open-pollination in a controlled environment in Grand Haven, Michigan.

Asexual reproduction of the new *Abelia* plant by softwood cuttings in a controlled greenhouse environment in Grand Haven, Michigan since the summer of 2019 has shown that the unique features of this new *Abelia* plant are stable and reproduced true to type in successive generations of asexual reproduction.

SUMMARY OF THE INVENTION

Plants of the new *Abelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNAMW'. These characteristics in combination distinguish 'SMNAMW' as a new and distinct *Abelia* plant:

1. Upright to outwardly spreading and mounding plant habit.
2. Moderately vigorous to vigorous growth habit.
3. Freely branching habit; dense and bushy appearance.
4. Dark green-colored leaves that in the autumn, turn yellow to bright red and burgundy in color.
5. Freely flowering habit.
6. Strongly fragrant white-colored flowers and reddish pink-colored corolla tubes.
7. Good garden performance.

Plants of the new *Abelia* can be compared to plants of the female parent selection. In side-by-side comparisons, plants of the new *Abelia* differ primarily from plants of the female parent selection in the following characteristics:

1. Plants of the new *Abelia* are more freely branching than plants of the female parent selection.
2. Plants of the new *Abelia* are more compact, denser and bushier than and not as open and rangy as plants of the female parent selection.

Plants of the new *Abelia* can also be compared to plants of *Abelia mosanensis* 'SMNAMDS', disclosed in U.S. Plant Pat. No. 27,370. In side-by-side comparisons, plants of the new *Abelia* differ primarily from plants of 'SMNAMDS' in the following characteristics:

1. Plants of the new *Abelia* are more freely branching than plants of 'SMNAMDS'.
2. Plants of the new *Abelia* are more compact, denser and bushier than and not as open and rangy as plants of 'SMNAMDS'.
3. During the autumn, leaves of plants of the new *Abelia* are more vibrant in color than leaves of 'SMNAMDS'.

BRIEF DESCRIPTION OF THE PHOTOGRAPHS

The accompanying colored photographs illustrate the overall appearance of the new *Abelia* plant showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet (FIG. 1) is a side perspective view of a typical flowering plant of 'SMNAMW' grown in a container.

Figure 2:
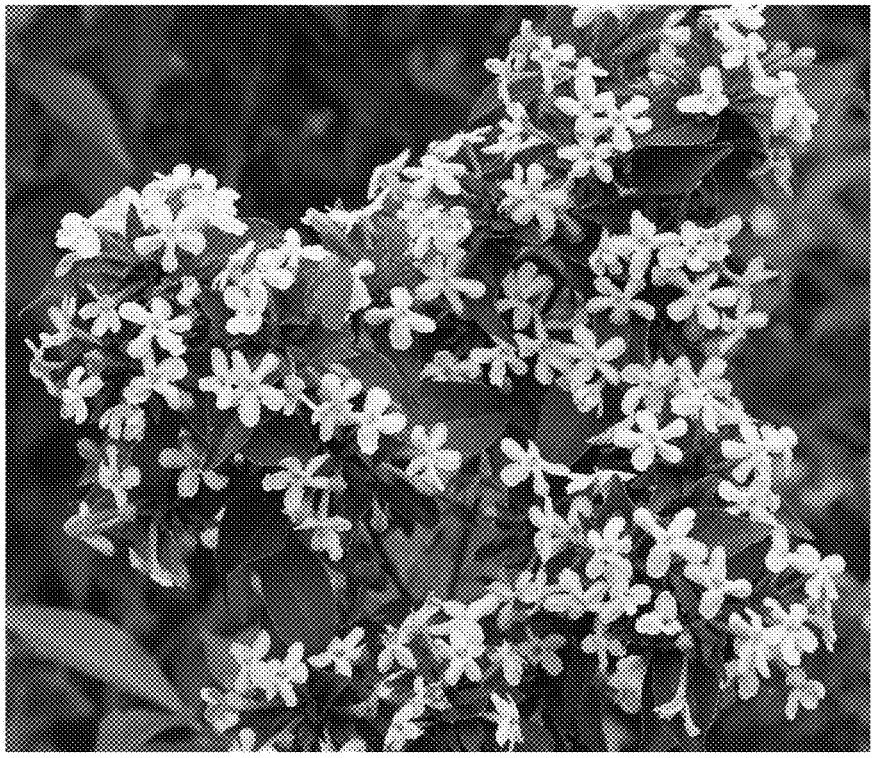

The photograph on the second sheet (FIG. 2) is a close-up view of typical flowers of 'SMNAMW'.

Figure 3:
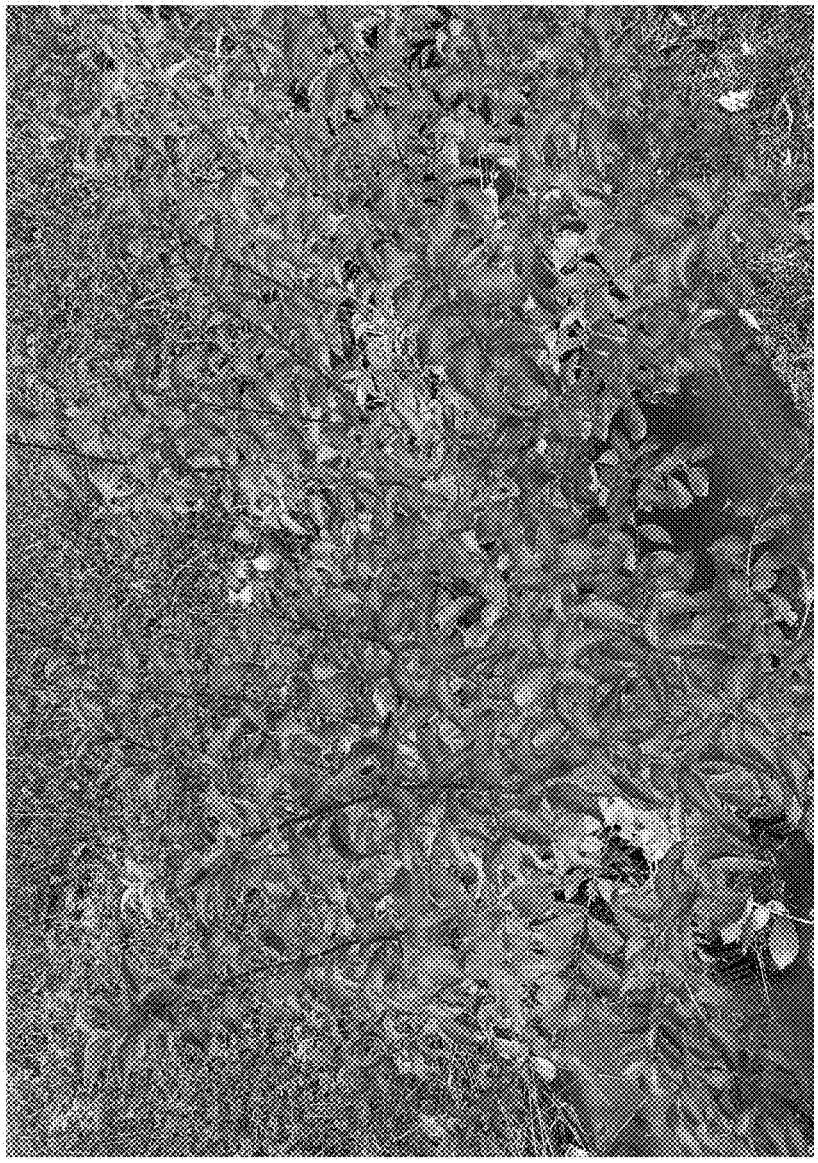

The photograph on the third sheet (FIG. 3) is a side perspective view of typical plant of 'SMNAMW' grown in an outdoor nursery during the autumn.

DETAILED BOTANICAL DESCRIPTION

The following observations, measurements and values describe plants grown during the late spring and early summer in two-gallon containers in a polyethylene-covered greenhouse in Grand Haven, Michigan and under cultural practices typical of commercial *Abelia* production. During the production of the plants, day temperatures ranged from 18° C. to 27° C. and night temperatures ranged from 5° C. to 10° C. Plants were five years old when the photographs were taken and two years old when the description was taken. In the description, color references are made to The Royal Horticultural Society Colour Chart, 2015 Edition, except where general terms of ordinary dictionary significance are used.

Botanical classification: *Abelia mosanensis* 'SMNAMW'.

Parentage:

*Female, or seed, parent*.—Unnamed proprietary selection of *Abelia mosanensis*, not patented.

*Male, or pollen, parent*.—Unknown proprietary selection of *Abelia mosanensis*, not patented.

Propagation:

*Type*.—By softwood cuttings.

*Time to initiate roots, summer*.—About 40 days at temperatures ranging from 18° C. to 27° C.

*Time to produce a rooted young plant, summer*.—About 50 days at temperatures ranging from 18° C. to 27° C.

*Root description*.—Medium in thickness and fleshy; typically brown to off-white in color, actual color of the roots is dependent on substrate composition, water quality, fertilizer, substrate temperature and physiological age of roots.

*Rooting habit*.—Freely branching habit; dense.

Plant description:

*Plant form and growth habit*.—Perennial shrub; upright to outwardly spreading and mounding plant habit; moderately vigorous to vigorous growth habit and moderate to rapid growth rate.

*Branching habit*.—Freely branching habit, compact, dense and bushy growth habit with about 20 primary lateral branches each with numerous secondary lateral branches developing per plant.

*Plant height*.—About 50 cm.

*Plant diameter* (*area of spread*).—About 70 cm.

Lateral branch description:

*Length*.—About 35 cm.

*Diameter*.—About 2 mm.

*Internode length*.—About 3.5 cm.

*Strength*.—Strong.

*Aspect*.—About 10° to 30° from vertical.

*Texture, developing*.—Smooth glabrous.

*Texture, fully developed*.—Woody.

*Color, upper surface*.—Close to 176B.

*Color, lower surface*.—Close to 145A.

Leaf description:

*Arrangement*.—Opposite, simple.

*Length*.—About 6 cm.

*Width*.—About 2.5 cm.

*Shape*.—Elliptic.

*Apex*.—Acuminate.

*Base*.—Attenuate.

*Margin*.—Entire.

*Texture, upper surface*.—Smooth, glabrous and coriaceous.

*Texture, lower surface*.—Smooth, glabrous and coriaceous; raised venation.

*Venation pattern*.—Pinnate.

*Color*.—Developing leaves, upper and lower surfaces: Close to 144A; at the margins and apex, close to 177A. Fully expanded leaves, upper surface: Close to 147A; venation, close to 144A; in the autumn, colors vary from 162A, 179A and 176A. Fully expanded leaves, lower surface: Close to 147B; midvein, close to 147D and lateral venation, close to NN137A; in the autumn, colors vary from 162A, 179A and 176A.

*Petioles*.—Length: About 2 mm. Diameter: About 2 mm. Texture, upper and lower surfaces: Smooth, glabrous. Color, upper surface: Close to 144A. Color, lower surface: Close to 147D.

Flower description:

*Flower appearance and arrangement*.—Single salver-form flowers arranged in terminal clusters; freely flowering habit with about eight to ten flowers per cluster and numerous flowers developing per plant during the flowering season; flower face upright to outwardly.

*Fragrance*.—Strongly fragrant; jasmine-like.

*Natural flowering season*.—Plants flower in May and June in Michigan; individual flowers last about one to two weeks on the plant; flowers not persistent.

*Flower buds*.—Length: About 1.8 cm. Diameter: About 5 mm. Shape: Spatulate. Color: Close to 52A to 52B.

*Flower diameter*.—About 1.5 cm.

*Flower depth*.—About 1.7 cm.

*Flower throat diameter*.—About 5 mm.

*Flower tube length*.—About 1.2 cm.

*Flower tube diameter, proximally*.—About 2 mm.

*Petals*.—Quantity and arrangement: Five fused petals arranged in a single whorl and fused at the base into a slender tube. Lobe length: About 7 mm. Lobe width: About 5 mm. Shape: Elliptic. Apex: Obtuse. Base: Fused. Margin: Entire. Texture, upper and lower surfaces, lobes: Smooth, glabrous; somewhat fleshy. Texture, throat: Smooth, glabrous; somewhat fleshy. Texture, tube: Smooth, glabrous; somewhat fleshy. Color: When opening, upper and lower surfaces: Close to NN155C with apices, tinged with close to 65D. Fully opened, upper and lower surfaces: Close to NN155D. Throat: Close to NN155D. Tube: Close to 52A to 52B.

*Sepals*.—Quantity and arrangement: Five sepals arranged in a single whorl. Length: About 9 mm. Width: About 3 mm. Shape: Narrowly elliptic to oblanceolate. Apex: Acute. Base: Cuneate. Margin:

Entire. Texture, upper and lower surfaces: Smooth, glabrous. Color, upper and lower surfaces: Close to 144A; color becoming closer to 182A with subsequent development.

*Peduncles*.—Length: About 4 mm. Diameter: About 1 mm. Strength: Strong. Aspect: About 45° to 90° from stem axis. Texture: Smooth, glabrous. Color: Close to 144B.

*Reproductive organs*.—Stamens: Quantity per flower: Five Filament length: Less than 1 mm; mostly adnate to the throat. Filament color: Close to NN155D. Anther length: About 1 mm. Anther shape: Oblong. Anther color: Close to 158D. Pollen amount: Sparse. Pollen color: Close to 158D. Pistils: Quantity per flower: One. Pistil length: About 1.5 cm. Stigma shape: Hemispherical to peltate. Stigma color: Close to 144A. Style length: About 1.4 cm. Style color: Close to 155C. Ovary color: Close to 144B. Seeds and fruits: To date, seed and fruit production have not been observed on plants of the new *Abelia*.

Garden performance: Plants of the new *Abelia* have been observed to have good garden performance and to tolerate rain, wind and to be suitable for USDA Zones 4 through 8.

Pathogen & pest resistance: To date, plants of the new *Abelia* have not been shown to be resistant to pathogens and pests common to *Abelia* plants.

It is claimed:

1. A new and distinct *Abelia* plant named 'SMNAMW' as herein illustrated and described.

* * * * *